(12) United States Patent
Metivier et al.

(10) Patent No.: US 9,371,306 B2
(45) Date of Patent: Jun. 21, 2016

(54) CYCLIC (POLY)GLYCEROL SULPHATES AND PREPARATION AND USE THEREOF

(75) Inventors: Pascal Metivier, Shanghai (CN); Yan Zhao, Shanghai (CN); Zhaoyu Fan, Shanghai (CN); Chenjiang Zhu, Shanghai (CN)

(73) Assignee: Rhodia Operations, Aubervillers (FR)

( * ) Notice: Subject to any disclaimer, the term of this patent is extended or adjusted under 35 U.S.C. 154(b) by 68 days.

(21) Appl. No.: 14/356,512

(22) PCT Filed: Nov. 10, 2011

(86) PCT No.: PCT/CN2011/082043
§ 371 (c)(1),
(2), (4) Date: May 6, 2014

(87) PCT Pub. No.: WO2013/067700
PCT Pub. Date: May 16, 2013

(65) Prior Publication Data
US 2015/0299158 A1 Oct. 22, 2015

(51) Int. Cl.
*C07D 327/10* (2006.01)

(52) U.S. Cl.
CPC ................................. *C07D 327/10* (2013.01)

(58) Field of Classification Search
CPC .................................................... C07D 327/10
See application file for complete search history.

(56) References Cited

U.S. PATENT DOCUMENTS

| | | | |
|---|---|---|---|
| 4,824,867 A | 4/1989 | Smith et al. | |
| 5,348,557 A | 9/1994 | Von Der Eltz et al. | |
| 2010/0063302 A1 | 3/2010 | Muraoka et al. | |

FOREIGN PATENT DOCUMENTS

| | | |
|---|---|---|
| CA | 2060079 A1 | 8/1992 |
| CN | 1087694 A | 6/1994 |
| DE | 1804810 A | 6/1970 |
| FR | 2021490 A1 | 7/1970 |
| JP | 2003238556 A | 8/2003 |
| WO | WO 2013067915 A1 | 5/2013 |

OTHER PUBLICATIONS

Ko, S. Y., "An Access to erythro-Diols via Sharpless's Asymmetric Dihydroxylation Reaction." The Journal of Organic Chemistry 59.9 (1994): 2570-2576.*
Parris, N., et al—"Soap-Based Detergent Formulations: XVIII. Effect of Structure Variations on Surface-Active Properties of Sulfur Containing Amphoteric Surfactants", Mar. 1976, Journal of the American Oil Chemists' Society, vol. 53, pp. 97-100; 4 pgs.
Zhou, Tianhua , et al—"Synthesis and thermotropic liquid crystalline properties of zwitterionic gemini surfactants containing a quaternary ammonium and a sulfate group", 2009, Journal of Colloid and Interface Science, vol. 338, pp. 156-162; 7 pgs.
Sawed, Iliyas A., et al—"Asymmetric synthesis of aryloxypropanolamines via $OsO_4$-catalyzed asymmetric dihydroxylation", 2005, Science Direct, Tetrahedron, vol. 61, Elsevier, pp. 2831-2838; 8 pgs.
Kosaka, T., et al—"New Plant and New Applications of Sucrose Esters", 1976, Sucrochemistry: A Symposium Sponsored by the International Sugar Research Foundation, Inc., and by the Division of Carbohydrate Chemistry at the $172^{nd}$ Meeting of the American Chemical Society, San Francisco, CA, Aug. 31-Sep. 2, 1976; Published-1977, John Hickson, Editor, vol. 41, American Chemical Society, pp. 84-96; 14 pgs.
James, Catherine E., et al—"Sucrose and Its Derivatives", 1989, Progress in the Chemistry of Organic Natural Products, vol. 55, pp. 117-184; 70 pgs.
Kunz, Markwart—Sucrose-based Hyrdophilic Building Blocks as Intermediates for the Synthesis of Surfactants and Polymers, 1991, Carbohydrates as Organic Raw Materials, Frieder Lichtenthaler, Editor, Developed from a Workshop Sponsored by Sudzucker AG, at the Technische Hochschule Darmstadt, Apr. 11-12, 1990, Weinheim-VCH, pp. 127-153; 29 pgs.
U.S. Appl. No. 14/356,525, Pascal Metivier et al.

* cited by examiner

*Primary Examiner* — Samantha Shterengarts
*Assistant Examiner* — Matt Mauro
(74) *Attorney, Agent, or Firm* — Osha Liang LLP

(57) ABSTRACT

The present invention relates to novel cyclic sulphates of (poly)glycerol, particularly to the novel compound of 4-(hydroxymethyl)-1,3,2-dioxathiolane-2,2-dioxide. The present invention also relates to the preparation process of the cyclic sulphate compounds, and to the use thereof as an intermediate to prepare green surfactants containing sulphate groups.

20 Claims, 2 Drawing Sheets

$^1$H NMR (CDCl$_3$)

$^{13}$C NMR (CDCl$_3$)

CYCLIC (POLY)GLYCEROL SULPHATES AND PREPARATION AND USE THEREOF

CROSS-REFERENCE TO RELATED APPLICATIONS

This application is a U.S. national stage entry under 35 U.S.C. §371 of International Application No. PCT/CN2011/082043 filed Nov. 10, 2011, the whole content of this application being herein incorporated by reference for all purposes.

FIELD OF THE INVENTION

The present invention relates to a novel cyclic sulphate of glycerol or polyglycerols with free hydroxyl group, more particular to the novel compound of 4-(hydroxymethyl)-1,3,2-dioxathiolane-2,2-dioxide. The present invention also relates to the preparation process of the novel cyclic sulphate compounds, and to the use thereof as an intermediate to prepare surfactants containing sulphate groups.

BACKGROUND OF THE INVENTION

Most of the surfactants produced by the chemical industry are based on petrochemicals. Surfactants made from petrochemicals by some traditional processes contain 1,4-dioxane which may be carcinogenic to humans. A number of efforts to use carbohydrates as bulk raw materials for synthesis of non-ionic surfactants have been reported. See Kosaka, T; Yamada T. in *Sucrochemistry ACS Symposium Series*, No. 41; John L. Hickson, Ed.; Am. Chem. Soc.: Washington, D.C., 1977, p 84; James, C. E.; Hough, L.; Khan, R. *Prog. Chem. Org. Natl. Products* 1989, 55, 117; and Kunz, M. in *Carbohydrates as Organic Raw Materials*. F. W. Lichtenthaler, Ed.; VCH: Weinheim, 1991, p 127. There has been a rapidly increasing demand for green surfactants, especially for those containing sulphate group(s).

Conventionally, most of the chemists use protected cyclic sulfites to prepare corresponding cyclic sulphates via oxidation, in which the starting compounds do not have free primary hydroxyl group or such group needs to be protected before the oxidation. See Hiyas A. Sayyed et al., *Tetrahedron* 61 (2005) 2831-2838. It is necessary to remove the protection group to free a hydroxyl group for further reaction. For the cyclic sulfites containing primary hydroxyl groups, there is as yet no one-step-process of converting them into the corresponding cyclic sulphates with high yield, simultaneously without affecting the hydroxyl groups. Thus, there is still a need for an improved process to prepare cyclic sulphates.

SUMMARY OF THE INVENTION

Item 1. The present invention relates to a cyclic (poly) glycerol sulphate compound of formula (I):

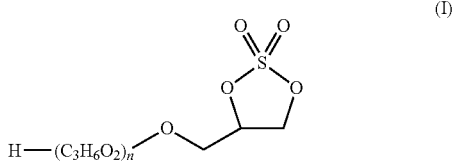

wherein n is an integer from 0 to 20; and each —C$_3$H$_6$O$_2$— is independently a glycerol residual.

Item 2. The compound according to item 1, wherein n is 0-10.

Item 3. The compound according to item 1 or 2, wherein n is 0-4.

Item 4. The compound according to item any one of the preceding items, wherein each —C$_3$H$_6$O$_2$— is independently

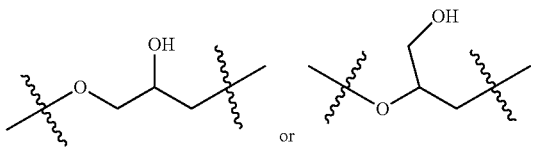

Item 5. The compound according to any one of the preceding items, wherein n is 0 and the compound of formula (I) is the compound of the following formula (I')

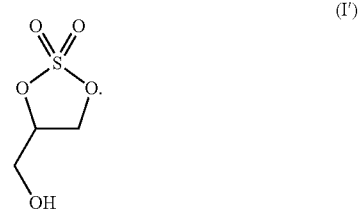

Item 6. The present invention further relates to a process for preparing a compound according to any one of the preceding items, comprising the step of reacting a compound of formula (II) with an oxidant

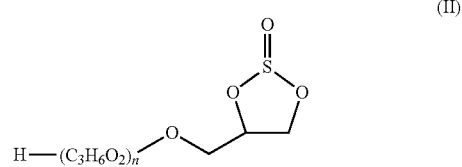

wherein n and —C$_3$H$_6$O$_2$— are as defined in any one of the preceding items.

Item 7. The process according to the preceding item, wherein n is 0 and the compound of formula (II) is the compound of the following formula (II')

Item 8. The process according to item 6 or 7, wherein the oxidant is selected from the group consisting of KMO4/H3O$^+$, RuO4, RuO2/NaIO4, RuCl3.3H2O/NaIO4, Ca(MO4)2 and Ba(MnO4).

Item 9. The process according to item 6 or 7, wherein the oxidant is a ruthenium-based oxidant system comprising a catalytic amount of a ruthenium compound and a second agent that oxidizes the ruthenium compound to complete the catalyst cycle.

Item 10. The process according to item 9, wherein said ruthenium compound is selected from the group consisting of RuO2, RuCl3 and hydrates thereof and a mixture thereof; preferably RuCl3.3H2O or RuO2.

Item 11. The process according to any one of items 9-10, wherein said second agent is selected from the group consisting of hydrogen peroxide, periodate, permanganate, hypochlorite, bromate, peracetic acid, periodic acid, oxygen, cerium sulfate, electrochemically generated chlorine, and monoperoxysulfate; preferably NaIO4, KMnO4, NaClO or a mixture thereof.

Item 12. The process according to any one of items 9-11, wherein the said ruthenium compound and said second agent are used in the molar ratio of about 1:10-1:500, preferably about 1:50-1:300, more preferably about 1:100.

Item 13. The process according to any one of items 9-12, wherein the molar ratio of the cyclic sulfite of formula (II) and the ruthenium compound is about 1:0.0001 to 1:0.01; preferably about 1:0.001 to 1:0.005.

Item 14. The process according to any one of the preceding items, wherein the reaction carried out in a solvent system that is polar or non-polar.

Item 15. The process according to item 14, wherein said solvent system is a mixture of water and acetonitrile.

Item 16. The process according to any one of items 6-15, wherein the reaction is carried out under the temperature between about 0° C. to about 100° C., preferably around the room temperature.

Item 17. Use of a compound according any one of items 1-5 in the preparation of a surfactant containing sulphate moiety.

Item 18. A solution of a compound of formula (I) as defined in any one of claims 1-5 in THF.

Item 19. The solution according to item 18, wherein the compound is compound of formula (I').

DETAILED DESCRIPTION OF THE INVENTION

Figure 1:
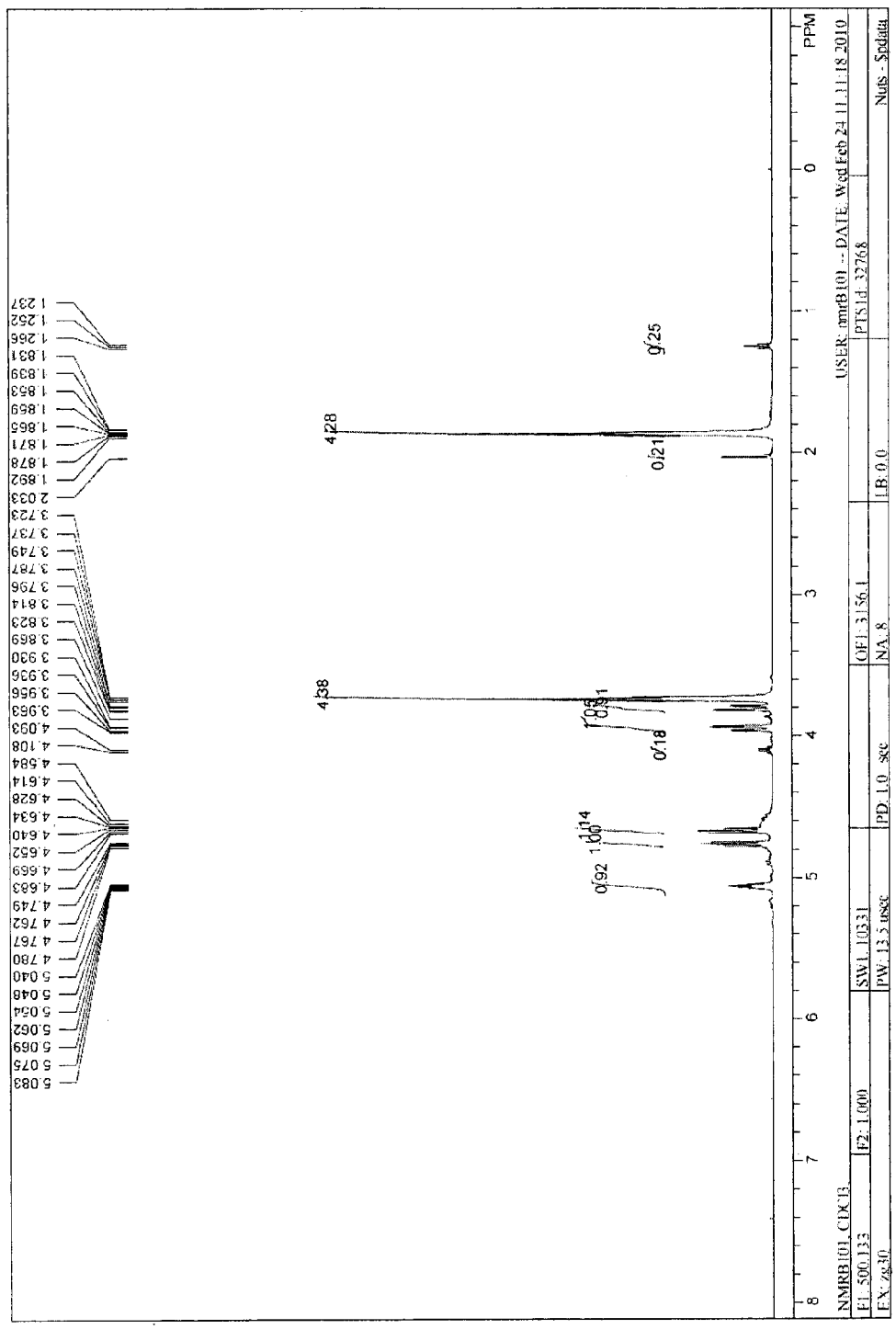
FIG. 1 is the $^1$H NMR (CDCl$_3$) spectra of the cyclic sulphate of formula (I')

The present invention relates to novel cyclic sulphates of (poly)glycerols. These compounds are useful as intermediates for preparing green surfactants.

Particularly, the present inventions relates to a cyclic (poly) glycerol sulphate compound of formula (I):

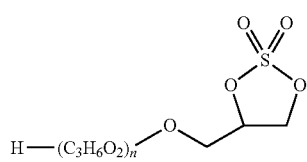

(I)

wherein n is an integer from 0 to 20; and each —C$_3$H$_6$O$_2$— is independently a glycerol residual.

In formula (I), the number (n) of glycerol residual —C$_3$H$_6$O$_2$— can be any integer from 0 to 20, i.e., 0, 1, 2, 3, 4, 5, 6, 7, 8, 9, 10, 11, 12, 13, 14, 15, 16, 17, 18, 19 or 20.

Preferably, n is an integer from 0 to 10, more preferably n is from 0 to 4, and most preferably n is 0.

In formula (I), each of the glycerol residual —C$_3$H$_6$O$_2$— can be independently one of the following groups:

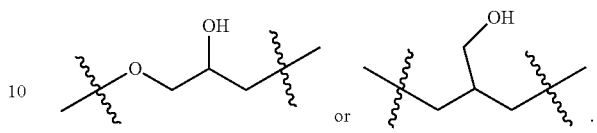

Therefore, the polyglycerol part of the compound of Formula (I) can be a homopolymer of any one of the above —C$_3$H$_6$O$_2$— block or a copolymer of the two —C$_3$H$_6$O$_2$— blocks.

In a preferably aspect, the present invention provides a compound of formula (I') (4-(hydroxymethyl)-1,3,2-dioxathiolane-2,2-dioxide):

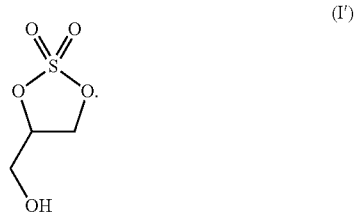

(I')

The compound of formula (I) and especially the compound of formula (I') contains an asymmetrical center. It can exist as (S) enantiomer or (R) enantiomer or any mixture thereof. The present invention relates to any one of these different forms of the compound or the mixtures. Particularly, the compounds of the invention contains sulphate group and free hydroxyl group simultaneously and can be used as an intermediate to synthesize the green surfactants.

Interestingly, it has been found now that the compounds of formula (I), especially the compound of formula (I') are considerably stable in tetrahydrofuran (THF) under normal storage conditions. Therefore, the present invention relates to a solution of a compound of formula (I) in THF. Particularly, the present invention relates to a solution of the compound of formula (I') in THF.

It is known in the art to use cyclic sulfites to prepare corresponding cyclic sulphates via oxidation. Therefore, the cyclic sulphates can be prepared by reacting corresponding cyclic sulfites with an oxidant. The oxidant can be for example KMO4/H3O$^+$, RuO4, RuO2/NaIO4, RuCl3.3H2O/NaIO4, Ca(MO4)2 or Ba(MnO4). Optionally, the free hydroxyl group(s) of the cyclic sulfites is/are protected before the oxidation and the protection group(s) is/are removed to free a hydroxyl group after the oxidation.

It has been surprisingly found that the cyclic sulfites containing primary hydroxyl groups can be oxidized into the corresponding cyclic sulphates with high yield, simultaneously without affecting the hydroxyl groups. Therefore, in another aspect, the present invention provides a process for the preparation of a compound of formula (I) of the present invention comprising the step of reacting a compound of formula (II)

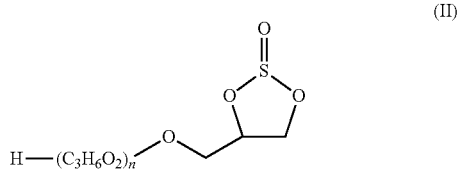

wherein n is an integer from 0 to 20; and each —C$_3$H$_6$O$_2$— is independently a glycerol residual,
with a ruthenium-based oxidant system comprising a catalyst amount of a ruthenium compound and second agent that oxidizes the ruthenium compound.

In formula (II), the number (n) of glycerol residual —C$_3$H$_6$O$_2$— can be any integer from 0 to 20, i.e., 0, 1, 2, 3, 4, 5, 6, 7, 8, 9, 10, 11, 12, 13, 14, 15, 16, 17, 18, 19 or 20. Preferably, n is an integer from 0 to 10, more preferably n is from 0 to 4, and most preferably n is 0.

In formula (II), each of the glycerol residual —C$_3$H$_6$O$_2$— can be independently one of the following groups:

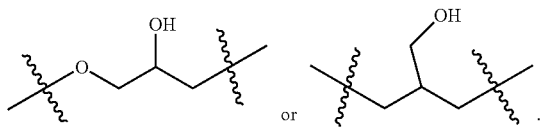 [SMILES: *CC(O)CO* ; *CC(C*)CO]

Therefore, the polyglycerol part of the compound of Formula (I) can be a homopolymer of any one of the above —C$_3$H$_6$O$_2$— block or a copolymer of the two —C$_3$H$_6$O$_2$— blocks.

In a preferably aspect, the compound of formula (II) is a compound of formula (II') (4-(hydroxymethyl)-1,3,2-dioxathiolane-2-oxide):

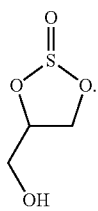

As used herein, the following definitions shall apply unless otherwise indicated.

As used herein, the term "sulfite" relates to the structure of

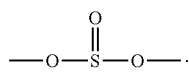

As used herein, the term "sulphate" relates to the structure of

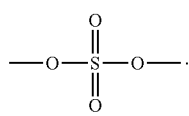

As used herein, the term "the second agent" refers to an oxidant that can oxidize a ruthenium compound used in the reaction of the invention. Preferably, the second agent can oxidize the ruthenium compound used in the reaction to complete the catalytic cycle.

The ruthenium-based oxidant system according to the present invention comprises, preferably essentially consisting of or consisting of a catalytic amount of a ruthenium compound and a second agent that oxidizes the ruthenium compound.

Preferably examples of the ruthenium compound according to the present invention are RuO4, ruthenium dioxide, ruthenium trichloride and hydrate thereof, more preferably RuCl$_3$.3H$_2$O.

Preferable examples of the second agent according to the present invention are hydrogen peroxide, periodate, permanganate, hypochlorite, bromate, peracetic acid, periodic acid, oxygen, cerium sulfate, electrochemically generated chlorine, and monoperoxysulfate. More preferably, the second agent according to the present invention is selected from the group comprising periodate, permanganate, hypochlorite, more preferably NaIO$_4$, KMnO$_4$, NaClO, and the mixture thereof.

Since ruthenium compound can be produced repeatedly when the oxidant system of the inventions is working, a catalytic amount of ruthenium compound is sufficient to complete the reaction of the present invention. Ruthenium compounds are generally expensive reagents and it is advantageously to use as less these reagents as possible. Preferably, the said ruthenium compound and said second agent are used in the mole ratio of 1:10-1:500, more preferably 1:50-1:300, most preferably 1:100.

Preferably, the molar ratio of the cyclic sulfite of formula (II) and the ruthenium compound is about 1:0.0001 to 1:0.01; more preferably about 1:0.001 to 1:0.005.

For the process of the present invention, there is no special requirement on the reaction conditions. Actually, the ruthenium-catalyzed oxidation reaction of the present invention can be carried out under mild conditions. For example, the oxidation reaction can be carried out in about 1 minutes to 1 hour in a solvent under a temperature from 0° C. to 100° C. The reaction temperature is preferably around room temperature. Preferably, the reaction will be completed in about 3-10 minutes.

The oxidation reaction of the present invention can be carried out in a solvent. The solvent can be either polar or non-polar. It is advantageous to use a solvent system consisted of an aqueous solvent(s) and an organic solvent(s). The aqueous solvents may be water or its mixture with methanol and/or ethanol. Said organic solvents are, for example, carbon tetrachloride, methylene chloride and/or acetonitrile. Preferably, said aqueous solvent is water.

Furthermore, the addition of acetonitrile to the solvent system significantly improves yields and shortens reaction time. Therefore, acetonitrile is a preferred organic solvent of the invention.

Additionally, it is advantageous to stir the reaction mixture throughout the course of the reaction to achieve good contact of the reaction components.

Yet another aspect of the present invention is the use of the compound of formula (I) as an intermediate in preparation of the surfactants containing sulphate moiety.

The compound of formula (II) can be prepared from (poly) glycerol and $SOCl_2$ as shown below.

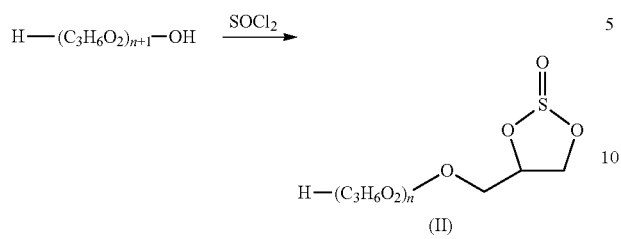

(II)

wherein n and —$C_3H_6O_2$— are as defined above.

Reference can be made, for example, to Tetrahedron 61 (2005) 2831-2838.

It is believed that dioxane cannot be formed during a process of producing surfactants based on cyclic sulphate. Also, a cyclic sulphate and surfactants based on the same can be 100% bio-based. A cyclic sulphate containing free hydroxyl group would be a very important intermediate the preparation of the green surfactants. Using this intermediate, one would not only be able to prepare lots of useful and new products containing sulphate, but also control the reaction position selectively to get the desired products.

The green surfactants obtained through the cyclic sulphate of the present invention can be used in many applications. For example, the surfactants can be used as pharmaceutical excipients such as a laxative in enemas, as an excipient on dissolvable caplets of, e.g., aspirins and other fiber therapy. The surfactants may also be used in detergents, fabric softeners, emulsions, paints, adhesives, inks, anti-fogs, ski waxes, snowboard wax, deinking of recycled papers, washing and enzymatic processes, agrochemical formulations, quantum dot coatings, biocides (sanitizers), cosmetics including shampoos, hair conditioners (after shampoo) and toothpastes.

EXAMPLES

The Examples which follow serve to illustrate the present invention in more detail without restricting the scope of the invention to the following embodiments by way of example.

The compound of formula (II') can be prepared from glycerol and $SOCl_2$ according to the method as described in Tetrahedron 61 (2005) 2831-2838. This compound is also commercially available from CHEMOS GmbH (CAS NO.: 13897-37-5). $NaIO_4$ is domestic, $RuCl_3.3H_2O$ is from Aldrich, $CH_3CN$ is from Merck.

Example 1

Process for Preparing the Compound of Formula (I')

A 250 mL three-necked round-bottom flask was charged with 6.9 g cyclic sulfite (4-(hydroxymethyl)-1,3,2-dioxathiolane-2-oxide (50 mmol)), 50 mL acetonitrile, 100 mg $RuCl_3.3H_2O$ (0.75 mmol) and 16 g $NaIO_4$ (75 mmol), the mixture was cooled down to 0~5° C. by ice-salt bath. Then 75 mL cooled water was added into the mixture, the temperature increased to 30° C. The mixture was stirred for 5 mins, the mixture became a green suspension. 400 mL ethyl acetate and 40 mL saturated $NaHCO_3$ aqueous solution were added into the mixture. The mixture was separated into two phases. The water phase was extracted by ethyl acetate (100 mL×2). The combined organic phase was washed by 40 mL water and dried by anhydrous $Na_2SO_4$. The solvent was removed with a rotary evaporator to yield 5.6 g yellow liquid desired product, crude yield: 72.7%.

$^1H$ NMR ($CDCl_3$, 500 MHz), δ: 5.05-5.08 (m, 1H), 4.75-4.78 (m, 1H), 4.63-4.68 (m, 1H), 3.95-3.96 (m, 1H), 3.80-3.82 (m, 1H) as shown in FIG. 1.

Figure 2:
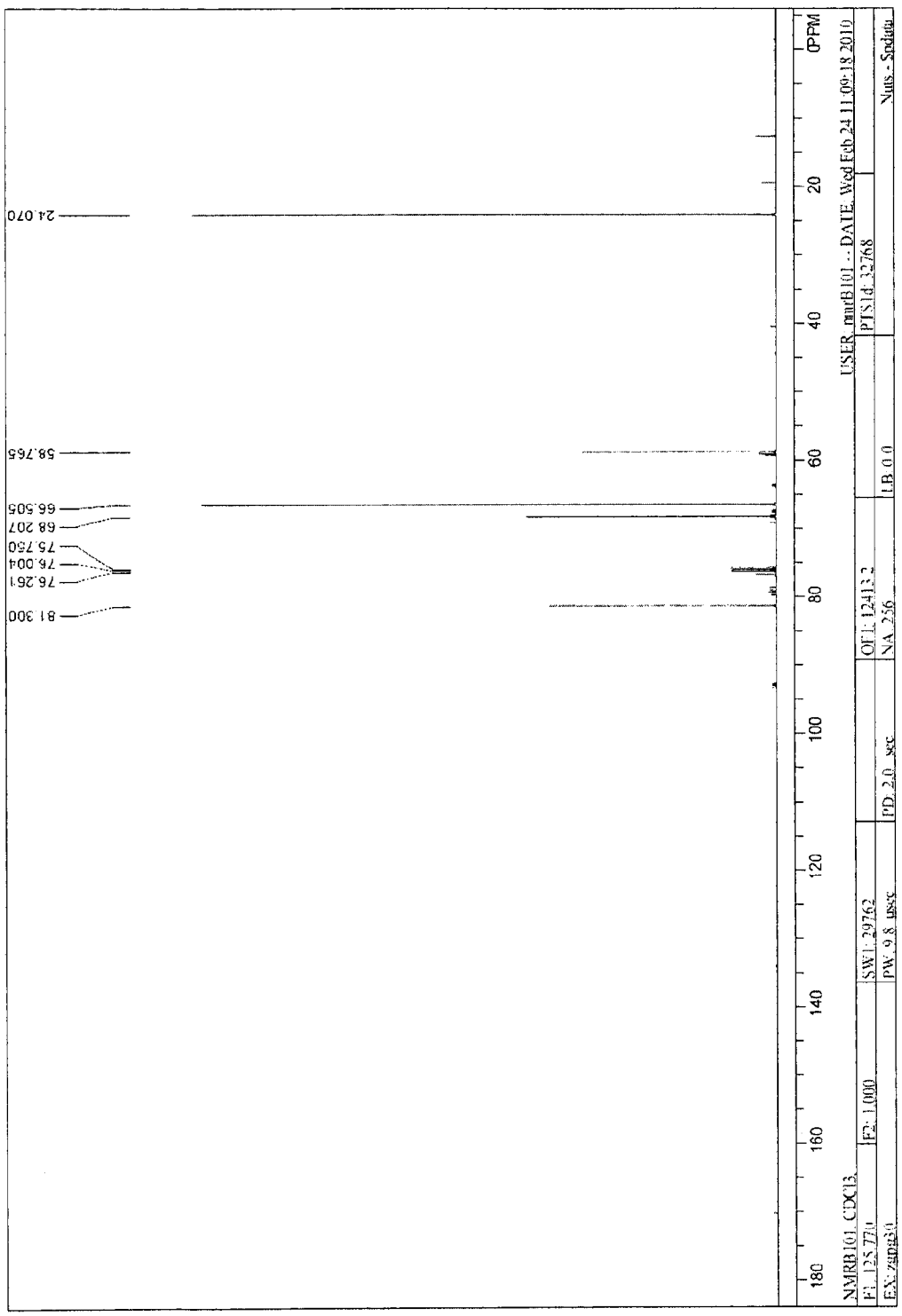
FIG. 2 is the $^{13}$C NMR (CDCl$_3$) spectra of the cyclic sulphate of formula (I').

$^{13}C$ NMR ($CDCl_3$, 500 MHz), δ: 81.3, 68.2, 58.7 as shown in FIG. 2.

Example 2

Process for Preparing Cyclic Diglycerol Sulphate

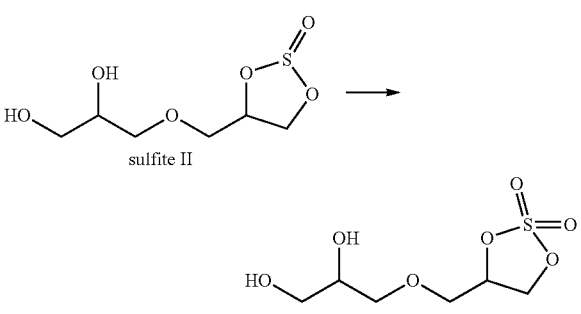

sulfite II

A 250 mL three-necked round-bottom flask was charged with sulfite II as shown above (50 mmol)), 50 mL acetonitrile, 100 mg $RuCl_3.3H_2O$ (0.75 mmol) and 16 g $NaIO_4$ (75 mmol), the mixture was cooled down to 05° C. by ice-salt bath. Then 75 mL cooled water was added into the mixture, the temperature increased to 30° C. The mixture was stirred for 5 mins, the mixture became a green suspension. 400 mL ethyl acetate and 40 mL saturated $NaHCO_3$ aqueous solution were added into the mixture. The mixture was separated into two phases. The water phase was extracted by ethyl acetate (100 mL×2). The combined organic phase was washed by 40 mL water and dried by anhydrous $Na_2SO_4$. The solvent was removed with a rotary evaporator to yield 6.0 g yellow liquid desired product, crude yield: 52.7%.

Example 3

Application Example 7.64 g of N, N-dimethyldodecan-1-amine and 25 ml of THF were charged into a 50 ml of three-necked round-bottomed flask, 5.36 g of CGS (compound of formula (I')) (in 10 ml of THF) was added dropwise into it in about 10 mins, then it was heated with an oil bath to reflux and stirred for sometime. Many bubbles were observed in the bottom of the flask. Then the reaction mixture was cooled to room temperature and filtered, washed with THF, and dried. 7.9 g of the following sulfate betaine as white solid was obtained.

$^1H$ NMR (DMSO-$d_6$) of the end product of this reaction ($CDCl_3$, 500 MHz), δ: 5.1 (m, 1H); 4.5 (m, 1H); 3.75 (m, 1H); 3.3-3.51 (m, 4H); 3.1 (d, 6H); 1.61-1.69 (m, 2H); 1.29 (m, 18H); 0.84 (t, 3H).

The invention claimed is:
1. A cyclic (poly)glycerol sulphate compound of formula (I):

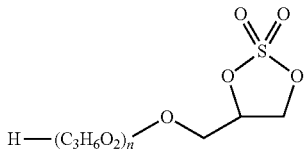

wherein n is an integer from 0 to 20; and each —C$_3$H$_6$O$_2$— is independently a glycerol residual.

2. The compound according to claim 1, wherein n is 0-10.
3. The compound according to claim 1, wherein n is 0-4.
4. The compound according to claim 1, wherein each —C$_3$H$_6$O$_2$— is independently

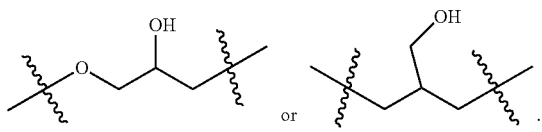 [SMILES: *CC(O)CO* ; *CC(C*)CO]

5. The compound according to claim 1, wherein n is 0 and the compound of formula (I) is the compound of the following formula (I')

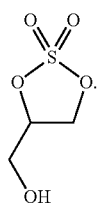

6. A solution of a compound of formula (I) as defined in claim 1 in THF.
7. The solution according to claim 6, wherein said compound is the compound of formula (I')

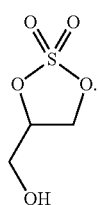

8. A method, comprising: using a compound according to claim 1 as an intermediate in the preparation of a surfactant containing sulphate moiety.
9. A process for preparing a compound according to claim 1, comprising the step of reacting a compound of formula (II) with an oxidant

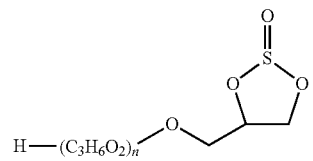

wherein n and —C$_3$H$_6$O$_2$— are as defined in claim 1.

10. The process according to claim 9, wherein n is 0 and the compound of formula (II) is the compound of the following formula (II')

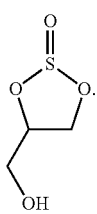

11. The process according to claim 9, wherein the oxidant is selected from the group consisting of KMnO4/H3O$^+$, RuO4, RuO2/NaIO4, RuCl3.3H2O/NaIO4, Ca(MnO4)2 and Ba(MnO4)2.

12. The process according to claim 9, wherein the oxidant is a ruthenium-based oxidant system comprising a catalytic amount of a ruthenium compound and a second agent that oxidizes the ruthenium compound to complete the catalyst cycle.

13. The process according to claim 12, further comprising reacting said ruthenium compound with the second agent, wherein the ruthenium compound is selected from the group consisting of RuO2, RuCl3 and hydrates thereof and a mixture thereof.

14. The process according to claim 12, wherein said second agent is selected from the group consisting of periodate, permanganate, hypochlorite, bromate, peracetic acid, periodic acid, oxygen, cerium sulfate, electrochemically generated chlorine, and monoperoxysulfate.

15. The process according to claim 14, wherein the periodate, the permanganate and the hypochlorite are selected from the group of NaIO4, KMnO4, NaClO and a mixture thereof.

16. The process according to claim 12, wherein said ruthenium compound and said second agent are used in the molar ratio of about 1:50-1:300.

17. The process according to claim 12, wherein the molar ratio of the cyclic sulfite of formula (II) and the ruthenium compound is about 1:0.0001 to 1:0.01.

18. The process according to claim 9, wherein the reaction carried out in a solvent system that is polar or non-polar.

19. The process according to claim 18, wherein said solvent system is a mixture of water and acetonitrile.

20. The process according to claim 9, wherein the reaction is carried out under the temperature between about 0° C. to about 100° C.

* * * * *